US006569092B1

(12) United States Patent
Guichon et al.

(10) Patent No.: US 6,569,092 B1
(45) Date of Patent: May 27, 2003

(54) METHOD AND SYSTEM FOR MONITORING ANIMALS

(76) Inventors: P. Timothy Guichon, Postal Bag 5, Bay 8, 87 Elizabeth Street, Okotoks, Alberta (CA), T0L 1T0; G. Kee Jim, Postal Bag 5, Bay 8, 87 Elizabeth Street, Okotoks, Alberta (CA), T0L 1T0; P. Bernard Kotelko, Box 57, Vegreville, Alberta (CA), T9C 1R1; Michael J. Kotelko, Box 57, Vegreville, Alberta (CA), T9C 1R1; Calvin W. Booker, Postal Bag 5, Bay 8, 87 Elizabeth Street, Okotoks, Alberta (CA), T0L 1T0; Yvonne T. G. Tollens, 47-1011 Canterbury Dr. S.W., Calgary, Alberta (CA), T2W 2S8

(*) Notice: Subject to any disclaimer, the term of this patent is extended or adjusted under 35 U.S.C. 154(b) by 0 days.

(21) Appl. No.: 09/275,598

(22) Filed: Mar. 24, 1999

Related U.S. Application Data

(63) Continuation-in-part of application No. 09/047,088, filed on Mar. 24, 1998, now Pat. No. 6,375,612.

(51) Int. Cl.[7] .................................................. A61B 5/00
(52) U.S. Cl. ........................ 600/300; 128/903; 128/920; 128/904; 119/455; 119/906; 705/3
(58) Field of Search ................................. 600/300–301, 600/529–538, 595; 128/920–925, 903, 904; 119/455, 51.02, 842

(56) References Cited

U.S. PATENT DOCUMENTS

| | | | |
|---|---|---|---|
| 4,448,150 A | 5/1984 | Catsimpoolas | |
| 4,618,861 A | 10/1986 | Gettens et al. | |
| 4,917,117 A | 4/1990 | Brom et al. | |
| 5,069,165 A | 12/1991 | Rousseau | |
| 5,315,505 A | 5/1994 | Pratt et al. | |
| 5,461,365 A | 10/1995 | Schlager et al. | |
| 5,474,085 A | 12/1995 | Harnik et al. | |
| 5,559,520 A | 9/1996 | Barzegar et al. | |
| 5,650,770 A | 7/1997 | Schlager et al. | |
| 5,663,734 A | 9/1997 | Krasner | |
| 5,673,647 A | 10/1997 | Pratt | |
| 5,867,820 A * | 2/1999 | Cureton et al. | ................. 705/1 |
| 6,000,361 A * | 12/1999 | Pratt | ....................... 119/51.02 |
| 6,032,084 A * | 2/2000 | Anderson et al. | ........... 700/241 |
| 6,113,539 A * | 9/2000 | Ridenour | .................... 600/300 |

FOREIGN PATENT DOCUMENTS

| | | |
|---|---|---|
| CA | 1311057 | 4/1989 |
| CA | 1296068 | 2/1992 |
| DE | 297 02 444 U1 | 5/1997 |
| EP | 0 624 313 A1 | 5/1994 |
| EP | 0 808 567 A1 | 5/1997 |
| GB | 2270405 | 3/1994 |
| WO | WO 97/24027 | 12/1996 |
| WO | WO 97/00708 | 1/1997 |

OTHER PUBLICATIONS

Arthur R. Rodger, Ph.D., Centre for Northern Forest Ecosystem Research, Ontario Ministry of Natural Resources, *Moose Guidelines Evaluation Program* (Oct. 15, 1997) http://www.cnfer.on.ca/moose–guide.htm.

B.F. Sowell, J.G.P. Bowman, C. Huisma, M.E. Branine, M.E. Hubbert, "Feeding Behavior of Feedlot Cattle," pp. 45–49.

Christine McClintic, Rollie Henkes, "Electronic Branding for Livestock".

* cited by examiner

*Primary Examiner*—Kevin Shaver
*Assistant Examiner*—Michael Astorino
(74) *Attorney, Agent, or Firm*—Piper Marbury Rudnick & Wolfe; Jefferson Perkins

(57) ABSTRACT

A method and system for tracking the movement of animals as the animals are moved from location to location during processing comprises the steps of tagging the animals under observation and tracking the location and duration each tagged animal spends at each location as it is moved to generate data representing each tagged animal's movement history

11 Claims, 12 Drawing Sheets

| RANCHERS | BACKGROUNDERS | FEEDERS | PACKER |
|---|---|---|---|
| R1: KAMLOOPS | B1: COCHRANE | F1: ACME | P1: HIGH RIVER |
| R2: KELOWNA | B2: CARDSTON | F2: VEGREVILLE | P2: MEDICINE HAT |
| R3: LETHBRIDGE | B3: TABER | F3: LANGDON | P3: CALGARY |
| R4: SWIFT CURRENT | B4: REGINA | F4: STRATHMORE | |

| ANIMAL HEALTH | |
|---|---|
| ANIMAL | DAYS ON FEED |
| A | 40 |
| B | 65 |
| C | 135 |
| D | 10 |
| • | • |
| • | • |
| • | • |

| ZONE DEFINITION | |
|---|---|
| FEEDLOT PEN A | |
| ZONE | XY COORDINATES |
| 14 | (DATA SET) |
| 16 | (DATA SET) |
| 18 | (DATA SET) |
| 20 | (DATA SET) |
| • | • |
| • | • |
| • | • |

FIG. 5A-1

| PHYSICAL CONDITION TABLE | | |
|---|---|---|
| ANIMAL HEALTH | RESPIRATORY DISORDER | REFERENCE MOVEMENT PATTERN DATA 1 |
| | GASTROINTESTINAL DISORDER | REFERENCE MOVEMENT PATTERN DATA 2 |
| | . . . | . . . |
| PERFORMANCE CHARACTERISTICS | YIELD GRADE 1 | REFERENCE MOVEMENT PATTERN DATA 10 |
| | YIELD GRADE 2 | REFERENCE MOVEMENT PATTERN DATA 11 |
| | . . . | . . . |
| | QUALITY GRADE PRIME | REFERENCE MOVEMENT PATTERN DATA 15 |
| | . . . | . . . |
| PRODUCTION CHARACTERISTICS | MARKET READY | REFERENCE MOVEMENT PATTERN DATA 20 |
| | . . . | . . . |

FIG. 5A-2

| | |
|---|---|
| REFERENCE MOVEMENT PATTERN DATA 1 | FREQUENCY WATER ZONE (HIGH) ≥ A<br>DURATION WATER ZONE (HIGH) ≥ B<br>FREQUENCY FOOD ZONE (LOW) ≤ C<br>DURATION FOOD ZONE (LOW) ≤ D<br>OVERALL ACTIVITY (LOW) ≤ E |
| REFERENCE MOVEMENT PATTERN DATA 2 | FREQUENCY WATER ZONE (HIGH) ≥ A<br>DURATION WATER ZONE (LOW) ≥ B<br>FREQUENCY FOOD ZONE (LOW) ≤ C<br>DURATION FOOD ZONE (LOW) ≤ D<br>⋮ |
| ⋮ | |
| REFERENCE MOVEMENT PATTERN DATA 10 | FREQUENCY FOOD ZONE (HIGH) ≥ A<br>DURATION FOOD ZONE (HIGH) ≥ B<br>DAYS ON FEED ≥ F |
| ⋮ | ⋮ |
| REFERENCE MOVEMENT PATTERN DATA 20 | FREQUENCY FOOD ZONE (MED) ≤ A<br>FREQUENCY FOOD ZONE (MED) ≥ C<br>DURATION FOOD ZONE (MED) ≤ B<br>DURATION FOOD ZONE (MED) ≥ D<br>DAYS ON FEED ≥ G |

FIG. 5B

| TAG NUMBER | X | Y | TIME | ZONE IN | ZONE FROM |
|---|---|---|---|---|---|
| A | $X_1$ | $Y_1$ | 11:01 | 14 | 20 |
| A | $X_2$ | $Y_2$ | 11:15 | 14 | 14 |
| A | $X_3$ | $Y_3$ | 11:25 | 14 | 14 |
| A | $X_4$ | $Y_4$ | 11:35 | 14 | 14 |
| A | $X_5$ | $Y_5$ | 11:45 | 16 | 14 |
| . | . | . | . | . | . |
| . | . | . | . | . | . |
| . | . | . | . | . | . |

FIG. 5C

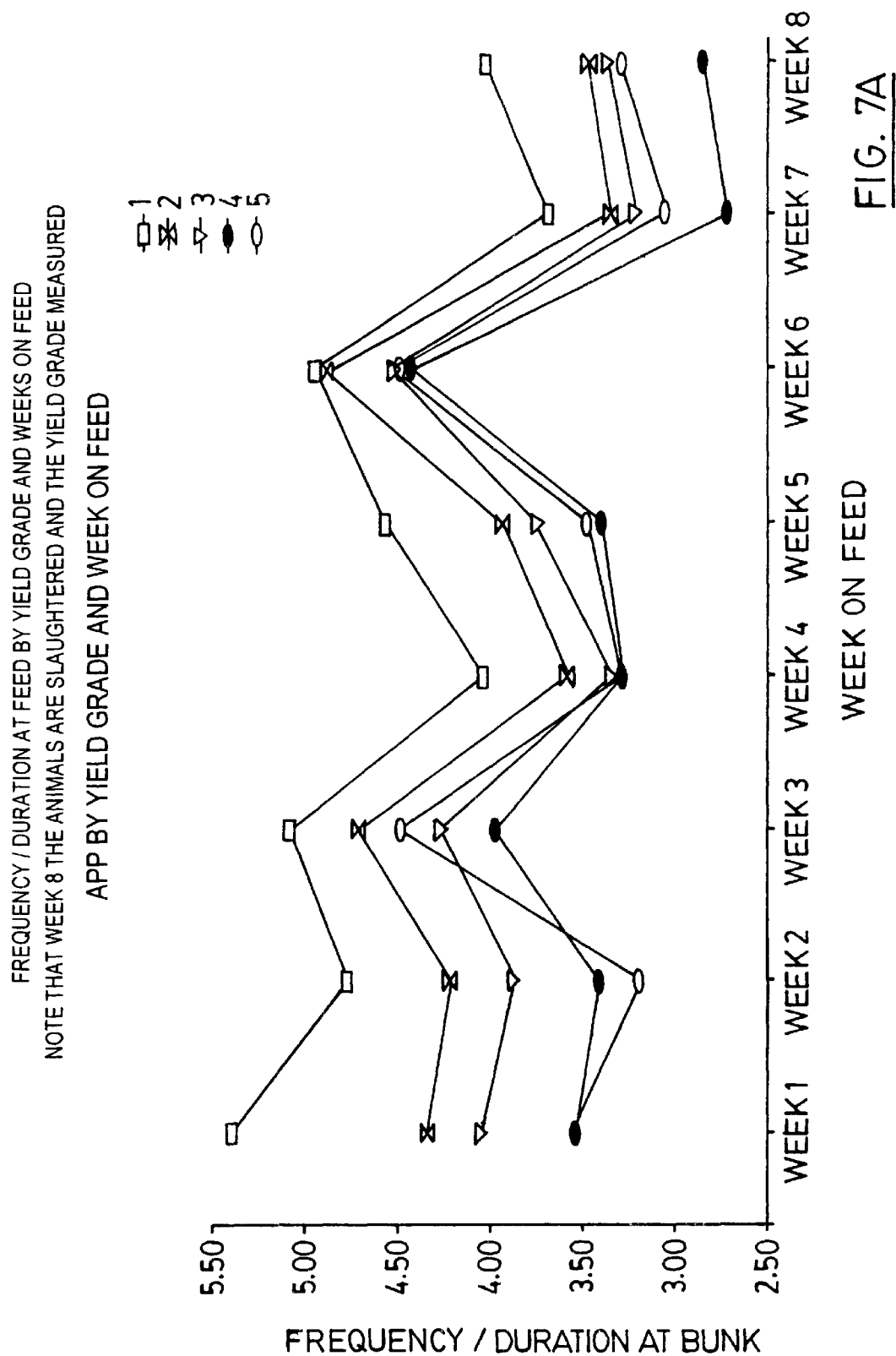

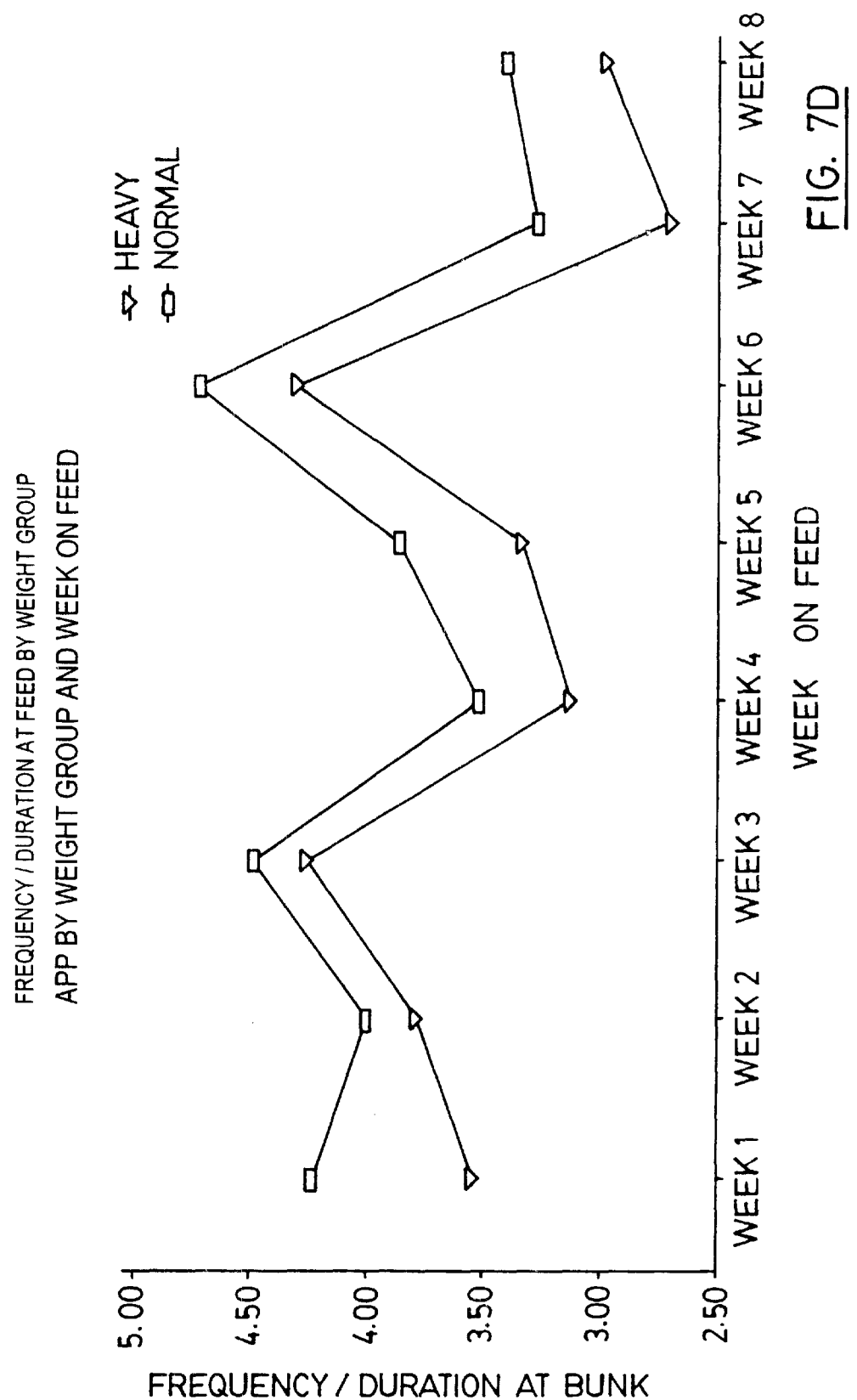

METHOD AND SYSTEM FOR MONITORING ANIMALS

RELATED APPLICATIONS

This application is a continuation-in-part of U.S. patent application Ser. No. 09/047,088 filed on Mar. 24, 1998 now U.S. Pat. No. 6,375,612 for an invention entitled "Method and System for Monitoring Animals".

FIELD OF THE INVENTION

The present invention relates to tracking systems and in particular to a system and method for monitoring the movement of animals within an area to determine at least one physical condition of the animals. The present invention also relates to a system and method for tracking livestock as they are prepared for slaughter.

BACKGROUND OF THE INVENTION

As is well known, livestock are typically bred at ranches. From the ranches the livestock may proceed to backgrounders for a period of time before being sent to feedlots for final preparation prior to slaughter by packers. The ranches, backgrounders, feedlots and packers are often geographically dispersed. At the feedlot, the livestock are processed in a hospital and processing area and treated with a variety of pharmaceuticals before being delivered to pens in the feedlot. In the feedlot pens, the animal's rations are varied at specific times to prepare the animals for slaughter. During the animal's stay in the feedlot, the animals are examined regularly by sight to detect sick animals as well as animals that appear ready for market. This requires individuals to move through the feedlot pens on horseback resulting in the livestock being disrupted and their stress levels increased.

When an animal is determined to be market ready, the animal is shipped to the slaughterhouse. At the slaughterhouse, the quality of the animal is evaluated by the packer based on one of two government standards, namely yield grade or quality grade. Yield grade is a measure of an animal's red meat to fat and bone ratio. Yield grade 1, the most attractive, has a high red meat to fat and bone ratio while yield grade 5, the least attractive, has a low red meat to fat and bone ratio. Quality grade is a measure of an animal's intra-muscular fat associated with quality. In the United States, the four quality grades of Prime, Choice, Select, and Standard. In Canada, the four corresponding quality grades are Prime, AAA, AA and A.

Ideally, animals that are shipped to the slaughterhouses meet high quality standards since penalties are imposed on feedlot operators for animals that do not meet quality standards. The tendency therefore, is for feedlot operators to put animals on feed for longer durations even though the animals may be considered market ready. This poses problems in that feed costs and methane or greenhouse gas production are increased.

When an animal at a feedlot is identified as being "sick", the animal is physically captured and taken to a hospital where the animal's temperature is taken to determine if in fact the animal is sick. Physically capturing the animal of course causes significant stress. If the animal is sick, the animal is treated with a range of antibiotics to cure any illnesses regardless of whether the animal requires treatment for all of these illnesses. If the animal is not sick, the animal is returned to the feedlot after having been stressed for no reason. Unfortunately, visual inspection of livestock to determine sickness is subjective making the accuracy of this method questionable. Also, significant lengths of time may elapse before sick animals show visual symptoms. As will be appreciated, this prior art method of monitoring livestock in a feedlot suffers may disadvantages.

Systems to monitor animals remotely to collect data concerning the condition of the animals are known. For example, U.S. Pat. No. 5,474,085 to Hurnik et al. discloses an apparatus for remote sensing of livestock using a thermographic imaging system. The thermographic imaging system remotely monitors the location, weight and temperature of livestock by taking thermographic images of the animals. The thermographic images are digitized and converted into number arrays. The number arrays are interpreted by software executed by a computer to provide animal weight information in a decipherable form.

Canadian Patent No. 1,296,068 to Friesen discloses a physiological monitoring system to measure physiological functions such as the pulse rate or temperature of an animal. The system includes a remote telemetry system carried by the animal including sensors to sense conditions of the animal and store data representing the sensed conditions. The stored data is then transmitted to a master telemetry system for processing.

In the article entitled "Feeding Behavior of Feedlot Cattle" authored by Sowell et al., a system to measure the feeding behavior of feedlot cattle by monitoring cattle at a feedbunk is described. The system includes passive radio frequency (RF) tags carried by the cattle. A read panel in close proximity to the feedbunk communicated with the RF tags carried by the cattle at the feedbunk to allow the presence and location of the cattle at the feedbunk to be recorded. The recorded information is processed to determine the average time untreated and treated cattle spend at the feedbunk.

Although the above-identified references discloses systems to monitor animals remotely, improved systems to provide information concerning the physical condition of animals within an area are desired.

It is therefore an object of the present invention to provide a novel method and system for monitoring animals within an area to determine at least one physical condition of the animals. It is also an object of the present invention to provide a novel method and system for tracking livestock as they are prepared for slaughter.

SUMMARY OF THE INVENTION

According to one aspect of the present invention there is provided a method for tracking the movement of animals as said animals are moved from location to location during processing comprising the steps of:

tagging each animal under observation; and tracking the location of each tagged animal and the duration each tagged animal spends at each location as it is moved to generate data representing each tagged animal's movement history.

Preferably, the generated data represents each tagged animal's movement history generally over its lifespan. It is also preferred that the locations include ranches, backgrounders, feedlots and packers.

In one embodiment, the generated data is used to detect tagged animals that have been in physical proximity with a tagged animal diagnosed with a transmittable disease. In another embodiment, the general data is used to detect locations that may be the cause of a trend exhibited by specific tagged animals.

Preferably, in at least one of the locations, the movement of animals within an area is monitored. During the monitoring, positional data of each animal under observation is collected. The positional data is processed to generate data representing the movement patterns of animals. The movement pattern data is then analzyed to determine at least one physical condition of the animals.

It is also preferred that the positional data is collected at intervals. During the analyzing step, the movement pattern data is compared with reference movement pattern data stored in a database representing typical movement patterns of animals exhibiting the at least one physical condition. The movement pattern data is compared with the reference movement pattern data to detect animals suspected of suffering a health problem.

According to still yet another aspect of the present invention there is provided a system for tracking the movement of tagged animals as said animals are moved from location to location during processing comprising:

at each location, a reader to read the tag on each of said animals thereat; and a processor in communication with said reader, said processor storing a record of each tagged animal's duration at said location.

The present invention provides advantages in that by tracking the livestock as they are prepared for slaughter data representing the livestock's movement history are generated. The data can be used to determine animals, which were in physical proximity of a diagnosed diseased animal thereby limiting the focus of animal testing. The data can also be used to determine locations, which may be the cause of trends exhibited by specific animals.

BRIEF DESCRIPTION OF THE DRAWINGS

Embodiments of the present invention will now be described more fully with reference to the accompanying drawings in which:

FIGS. 5a and 5b illustrate tables used in the system for feedlot management of FIG. 2;

FIG. 5c illustrates a virtual table created by the system for feedlot management during processing of data;

FIGS. 7a to 7d are graphs illustrating the frequency/duration of animals feeding vs. a number of different characteristics of interest.

DETAILED DESCRIPTION OF THE PREFERRED EMBODIMENTS

In general, the present invention relates to a system and method for monitoring the movement of animals within an area to determine at least one physical condition of the animals. The present inventors have found that the movement patterns of animals provide a wealth of information concerning their physical conditions including but not limited to animal health; performance characteristics such as yield grade, quality grade, back fat percentage, weight etc.; and production patterns such as market readiness, insufficient feeding, overfeeding, greenhouse gas emissions etc. During monitoring of the animals, data concerning the movement of each animal with a defined area is collected at intervals, processed and stored. Physical conditions definitions including reference movement pattern data representing typical movement patterns of animals having specific characteristics, traits, behaviors, and/or conditions etc. (hereinafter collectively referred to as "conditions") of interest, are also stored. The collected animal movement data is compared with the reference movement pattern data to allow animals to be classified according to these specific conditions of interest. This allows unhealthy animals to be detected quickly and treated and animals exhibiting other specific conditions of interest to be grouped. A preferred embodiment of the present invention will now be described more fully wherein the system and method are used to monitor the movement of animals, such as cattle, in a feedlot.

The present invention also relates to a method and system for tracking livestock generally throughout their lifespan as they are prepared for slaughter. As mentioned previously, most livestock are moved between geographically dispersed locations as they move from ranchers, backgrounders, feeders and finally to packers. The present inventors have found that by monitoring animals from the ranches to the packers, if an animal is determined to be sick, the treating of other animals can be limited to those animals that were in physical proximity to the sick animal. As a result, the scope of required testing can be significantly narrowed.

Figure 1:
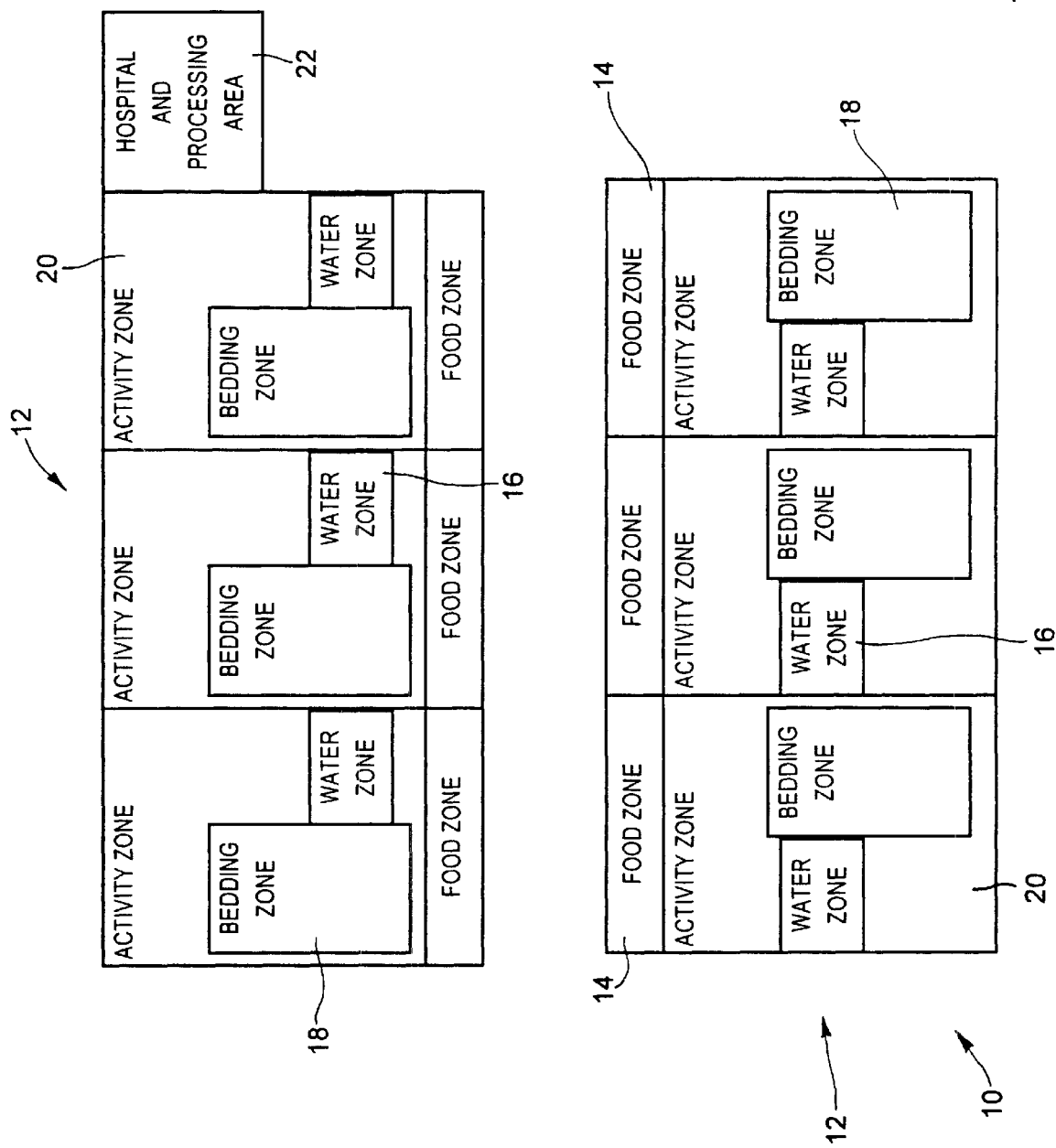
FIG. 1 is a diagram of a feedlot including a plurality of feedlot pens divided into a plurality of zones.

Referring now to FIG. 1, a feedlot is shown and is generally indicated to be reference numeral 10. As can be seen, the feedlot 10 includes a plurality of feedlot pens 12, each of which accommodates a plurality of animals (not shown). Each feedlot pen 12 is divided into a number of zones, namely a food zone 14, a water zone 16, a bedding zone 18 and an activity zone 20. Animals are free to move in the feedlot pens 12 between the various zones 14 to 20. A hospital and processing area 22 is also provided to treat sick animals removed from the feedlot pens 12 and to treat new animals entering the feedlot 10. In the present feedlot 10, the movement of each animal in its respective feedlot pen 12 is monitored and corresponding data is collected at intervals, processed and stored. In this manner, the number of times and duration each animal visits the various zones 14 to 20 within its feedlot pen 12 can be determined.

Figure 2:
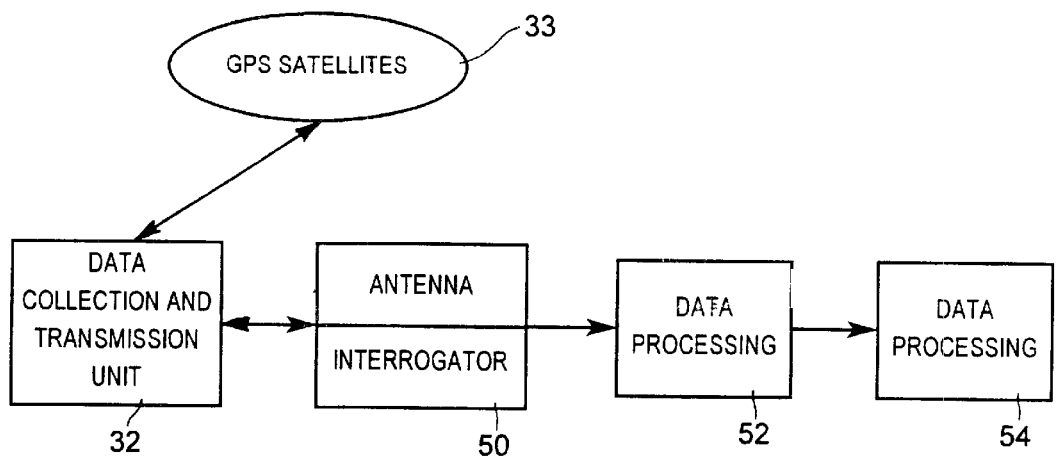
FIG. 2 is a block diagram of a system for feedlot management in accordance with the present invention.

In order to monitor the movement of the animals in each feedlot pen 12, each animal is fitted with a collar or tag (not shown) to which a data collection and transmission unit 32 is attached. (see FIGS. 2 and 3). The data collection and transmission unit 32 on the tag fitted to each animal is unique to that animal and stays with the animal during its entire stay in the feedlot 10. The data collection and transmission units 32 collect raw GPS data representing their positions from orbiting GPS satellites 33. The raw GPS data is accurate to about 100 m.

Figure 3:
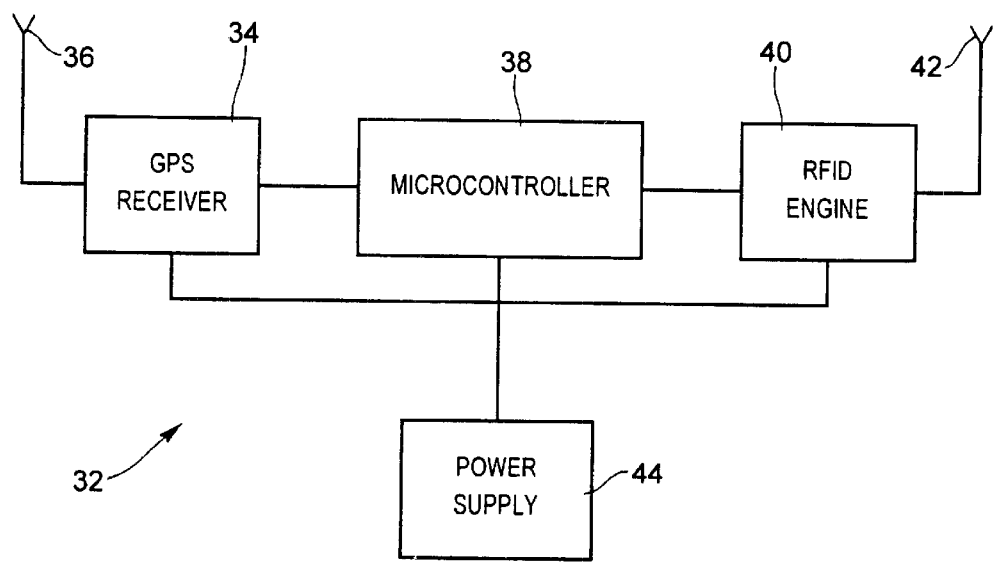
FIG. 3 is a block diagram of a data collection and transmission unit forming part of the system for feedlot management of FIG. 2.

Turning now to FIG. 3, one of the data collection and transmission units 32 is better illustrated. As can be seen, the data collection and transmission unit 32 includes a global positioning system (GPS) receiver 34 connected to an external antenna 36 and to a microcontroller 38 having resident memory. The microcontroller 38 is also connected to a radio frequency spread spectrum (RFID) engine 40 having an antenna 42. A power supply 44 is connected to the GPS receiver 34, microcontroller 38 and RFID engine 40.

Communicating with data collection and transmission units 32 on animal tags carried by animals in a plurality of feedlot pens 12, at user selected intervals, is an interrogator 50. The interrogator 50 also communicates with a data collection and transmission unit at a fixed location (not shown) to provide a field reference allowing GPS satellite signal propagation errors to be determined. A first processor 52 in the form of a Pentium® personal computer (PC) is connected to the interrogator 50. The processor 52 receives the raw GPS data from the Interrogator 50 and processes the raw GPS data to sub-metre accuracy. Thereafter the processor 52 converts the GPS data into XY coordinates and stores the XY coordinates in an animal observation table together with other relevant information as will be described.

A second processor 54, also in the form of a personal computer, is connected to the processor 52 via a local area or wide area network. The processor 54 receives the animal observation table from processor 52 at intervals. The processor 54 executes software to process the data in the animal observation table to allow animals to be classified according to specific conditions of interest as will be described. Although not shown, the processor 54 includes a graphical user interface (GUI) to allow the results of the classifications to be visually presented and manipulated as desired.

Stored within the processor 54 are a plurality of tables (best seen in FIG. 5*a*), namely a zone definition table, an animal health table and a physical condition table. The zone definition table includes data defining the zones of each feedlot pen 12 in XY coordinates. The data in the zone definition table can be edited as desired allowing the zones in the feedlot pens 12 to be reconfigured. The animal health table includes data indicating the number of days each animal has been on feed since the arrival of the animal at the feedlot 10. The physical condition table stores a plurality of definitions. Each definition includes reference movement pattern data representing the typical movement pattern of an animal exhibiting a specific physical condition of interest to which the animals under observation are to be compared. The physical condition table can be edited to add or remove definitions. Also, the reference movement patterned data for each definition can be edited to update the definitions when new data becomes available.

In the present embodiment, the physical condition definitions relate to animal health, performance characteristics, and production patterns including greenhouse gas emissions. The physical condition definitions relating to animal health include reference movement pattern data modeling the typical movement patterns of animals suffering respiratory, gastrointestinal and neurological disorders and exhibiting muscular skeletal injuries.

The physical condition definitions relating to performance characteristics include reference movement pattern data modeling the typical movement patterns of animals of different yield grades, different quality grades, different back fat percentages, and different weights as a function of days on feed.

The physical condition definitions relating to production patterns include reference movement pattern data modeling the typical movement patterns of animals that are market ready, overfed and underfed. The definitions in the physical condition table will now be described more fully.

Animal Health

Referring now to Table 2, the typical movement patterns of animals suffering from different health problems are set out. It has been determined that animals spending more time at the water zone and visiting the water zone more often while spending less time in the food zone and generally being overall less active are likely to be suffering one of several respiratory diseases. Reference movement pattern data modeling this movement pattern is stored as a definition in the physical condition table to allow animals exhibiting this movement pattern to be identified quickly. In this manner, early identification of animals suffering respiratory diseases can be achieved allowing animals to be treated in the hospital and processing area 22 quickly and returned to the feedlot 10.

It has also been determined that animals moving very little are likely to be suffering a muscular skeletal injury. Reference movement pattern data modeling this movement pattern is stored as a definition in the physical condition table to allow animals exhibiting this movement pattern to be identified quickly. In this manner, early identification of animals suffering muscular skeletal injuries can be achieved allowing animals to be treated quickly in the hospital and processing area 22 and returned to the feedlot 10. In addition, it has been determined that stationary animals or animals moving in a circle in one direction likely suffer neurological disorders. Reference movement pattern data modeling these movement patterns is stored as definitions in the physical condition table to allow animals exhibiting these movement patterns to be identified quickly. In this case, the animals can be shipped from the feedlot 10 early to reduce production costs.

It has also been determined that animals visiting the water zone often and for short durations or visiting the water zone infrequently and for short durations are likely to be suffering gastrointestinal disorders. Reference movement pattern data modeling these movement patterns is stored as definitions in the physical condition table to allow animals exhibiting these movement patterns to be identified quickly. Early detection of animals suffering gastrointestinal disorders can prevent animal death through treatment at the hospital and processing area 22.

Performance Characteristics

With respect to performance characteristics, it has been determined that yield grade and quality grade of cattle can be correlated to the frequency and duration cattle spend in the food zone of the feedlot pen 12. Referring now to FIG. 7*a*, a graph showing the frequency and duration cattle of different yield grades spend feeding over an eight week period is illustrated. As can been seen, cattle having a yield grade 1 consistently spend more time in the food zone and visit the food zone more other than cattle of other yield grades. Accordingly, cattle showing a pattern of higher frequency visits and longer duration visits in the food zone relative to other animals will have a better yield grade. Reference movement pattern data modeling the graphical data is stored as definitions in the physical condition table to allow animals to be classified according to yield grade and grouped if desired.

Figure 7B:
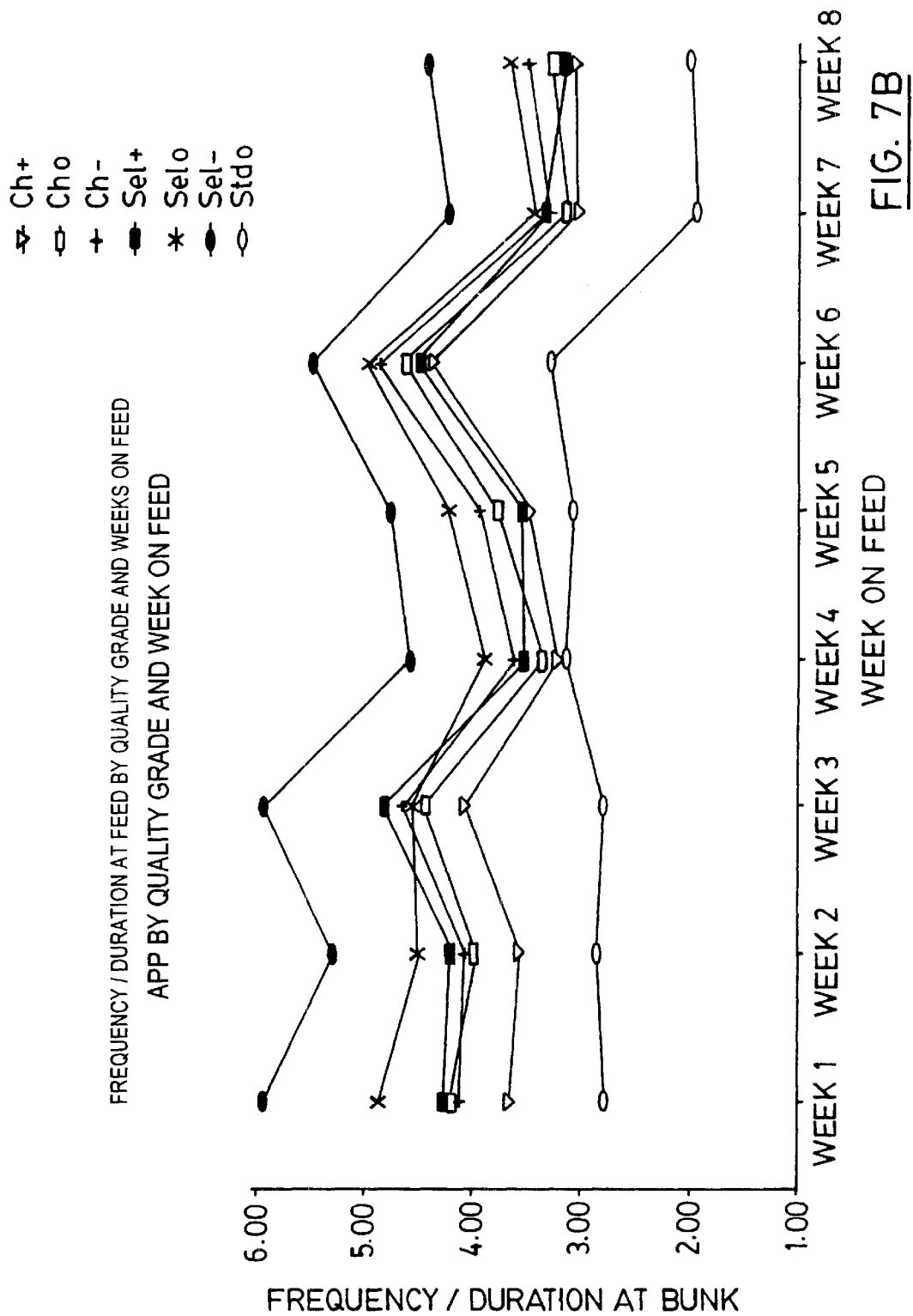

FIG. 7*b* shows a graph of the frequency and duration cattle of different quality grades spend in the food zone over an eight-week period. As can be seen, cattle having a high quality grade consistently spend less time in the food zone and visit the food zone less often than cattle of other quality grades. Reference movement pattern data modeling the graphical data is stored as definitions in the physical condition table to allow animals to be classified according to quality grade and grouped if desired.

Figure 7C:
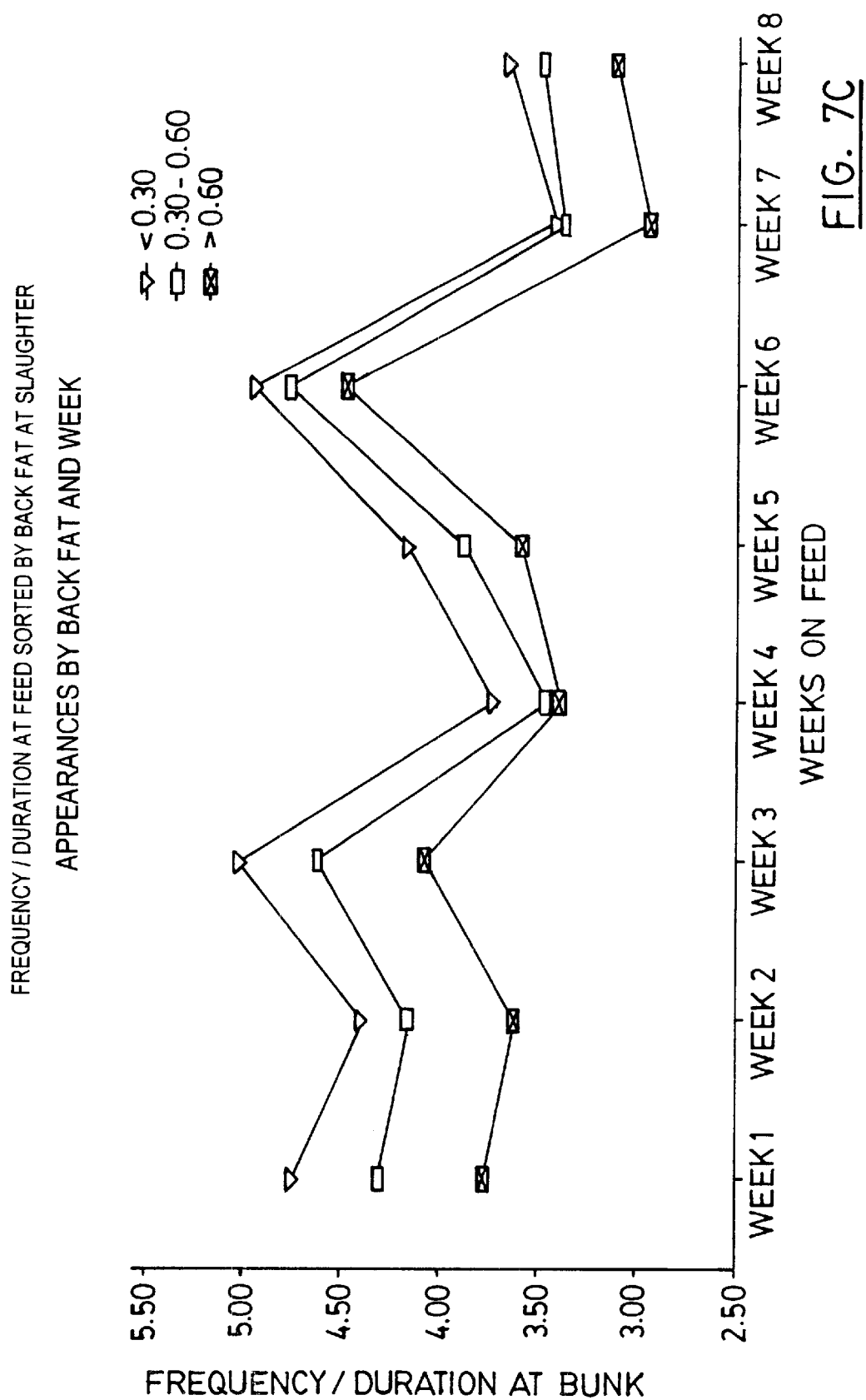

FIG. 7c shows a graph of the frequency and duration cattle having different amounts of back fat spend in the food zone over an eight-week period. As can be seen, cattle having less back fat consistently spend more time in the food zone and visit the food zone more often than cattle having more back fat. This is important since the amount of back fat carried by the animal will effect its yield grade. Reference movement pattern data modeling the graphical data is stored as definitions in the physical condition able to allow animals to be classified according to back fat percentage and grouped if desired.

FIG. 7d shows a graph of the frequency and duration cattle of different weight groups spend in the food zone over an eight-week period. As can be seen, cattle classified as "heavy" consistently spend less time in the food zone and visit the food zone less often than normal weight cattle. This is important since heavy animals are frequently discounted due to the fact that they are over fat and do not meet size and handling standards at slaughterhouses. Reference movement pattern data modeling the graphical data is stored as definitions in the physical condition table to allow animals to be classified according to weight and grouped if desired.

Production Patterns

With respect to production characteristics, animals spending less time in the food zone and visiting the food zone less nearing the end of their stay in the feedlot, can be identified as being market ready. This characteristic can be clearly seen in the graphs of FIGS. 7a and 7b. Reference movement pattern data modeling this movement pattern is stored as a definition in the physical condition table to allow animals showing this movement pattern to be identified quickly. Identified market ready animals can be shipped to slaughterhouses in a more timely manner. This maintains high performance standards in the feedlot by inhibiting animals from remaining in the feedlot too long. Animals remaining in the feedlot 10 while on feed too long tend to gain extra skeletal fat, which of course reduces performance. In addition, lengthening the stay of animals in the feedlot while on feed increases greenhouse gas emissions.

Definitions including reference movement pattern data modeling animal movement patterns where most animals move to the food zone when the feed truck passes or when few animals move to the food zone when the feed truck passes are also stored in the physical definition table. In the former case, insufficient feeding of animals having high energy requirements can be detected quickly and their feed rations adjusted accordingly. In the later case, overfeeding of animals can be detected quickly and their feed rations adjusted according to lower feed costs.

Referring now to FIG. 5b, some of the physical condition definitions are better illustrated. As can be seen, the reference movement pattern data includes threshold levels against which the movement patterns of the animals are compared. For example, in the case of the physical condition definition relating to respiratory disorders, the reference movement pattern data includes threshold levels to indicate high frequency and long duration visits to the water zone, low frequency and short duration visits to the food zone as well as overall low activity. The physical condition definition relating to gastrointestinal disorders has reference movement pattern data including threshold levels to indicate high frequency and short duration visits to the water zone and low frequency and short visits to the food zone.

The physical condition definition relating to yield grade 1 at a specific stage determined by days on feed has reference movement pattern data including threshold levels to indicate high frequency and long duration visits to the food zone as well as days on feed. The physical condition definition relating to market ready animals has reference movement pattern data including threshold levels to indicate medium frequency and medium duration visits to the food zone as well as days on feed. Animal movement pattern data is compared with these threshold levels to determine if the movement patterns of the animals meet the definitions.

The operation of the present method and system for monitoring animals will now be described.

When animals arrive in the feedlot in preparation for slaughter, the animals proceed through the feedlot 10 in stages. Typically, animals proceed through the feedlot in three stages, namely an early stage, a growth stage and a finish stage. Table 1, shows the time, ration, health protocol and animal movement patterns of interest during each stage. To improve performance of the feedlot, it is desired to identify and treat sick animals quickly, to classify animals according to one or more performance characteristics so that feed composition and rations can be adjusted accordingly, and to monitor production patterns so that market ready animals and undesired feedlot conditions can be detected quickly. The method and system according to the present invention provides for the above.

Figures 4, 8:
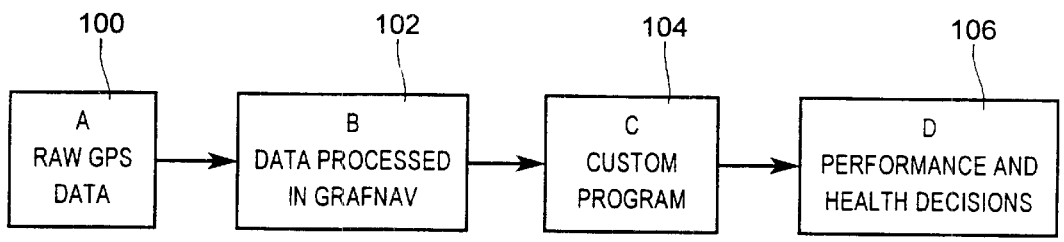
FIG. 4 is a flowchart illustrating data processing in the system for feedlot management of FIG. 2.
FIG. 8 is a table showing ranchers, backgrounders, feedlots and packers at geographically dispersed locations.

At selected intervals, in this case approximately every 15 seconds, the GPS receiver 34 in each data collection and transmission unit 32 is conditioned by the microcontroller 38 to poll the GPS satellites 33 and collect raw GPS data representing the associated animal's position within the feedlot pen 12 (see block 100 in FIG. 4). The raw GPS data is then conveyed to the microcontroller 38. When the microcontroller 38 receives the raw GPS data, it stores the raw GPS data in its resident memory together with a time startup.

The interrogator 50 is programmed to poll the data collection and transmission units 32 in a predetermined sequence to read the raw GPS data and time stamps stored therein at intervals. Specifically, the interrogator 50 continuously cycles through each data collection and transmission unit 32 in numerical order. If a data collection and transmission unit 32 cannot be read due to a lack of a clean line of sight, the interrogator 50 skips that data collection and transmission unit 32 and attempts to read it during the next cycle.

When a data collection and transmission unit is being read by the interrogator 50, the interrogator 50 sends an addressed command to that data collection and transmission unit 32 by way of a wireless RF communication link. When the RFID engine 40 in the data collection and transmission unit 32 receives the command, the command is passed to the microcontroller 38. Upon receiving the command, the microcontroller 38 responds to the command by sending the raw GPS data and time stamp stored in its resident memory to the RFID engine 40. The RFID engine 40 in turn transmits the raw GPS data and time stamp together with an identifier to the interrogator 50 via the wireless RF communications link. When the interrogator 50 receives the transmitted data from the data collection and transmission unit 32, it conveys the data to the processor 52.

When the processor 52 receives the raw GPS data, time stamp and identifier from one of the data collection and transmission units 32, the received data is processed using GrafNav software by Waypoint Consulting to increase the accuracy of the GPS data and is placed as an entry into the animal observation table (block 102). The time stamp is synchronized to GPS time and is adjusted for local time. The animal observation table in the present embodiment is in the form of an SQL database. Each entry made in the SQL database takes the form:

("Tag Number", "X", "Y", "Time"). where:

"Tag Number" is the data collection and transmission unit identifier;

"X" and "Y" represent the animal position either in latitude and longitude or in co-ordinates referenced to a survey point; and "Time" is the microcontroller time stamp.

Since the interrogator 50 continuously cycles through the data collection and transmission units 32, the SQL database is continuously updated at intervals to provide current and historical positional data concerning each of the animals in the feedlot pens 12. In this manner, a record of each animal's movement pattern within the feedlot pen 12 is maintained.

The processor 52, which communicates with the processor 54, downloads the SQL database to the processor 54 at predetermined intervals so that animal movement pattern data over a fixed time period is received by the processor 54. Once the SQL database has been downloaded, the processor 54 executes a routine and using the SQL database and the zone definition table creates a virtual table including the animal observation table entries together with current and previous zone position information (block 104). The entries in this virtual table take the form:

("Tag Number", "X", "Y", "Time", "Zone In", "Zone From") where:

"Zone In" represents the current zone position of the animal; and

"Zone From" indicates whether the animal has moved from one zone to another between successive entries in the table.

FIG. 5c illustrates an example of the virtual table for a single animal identified as "A". As can been seen, the Zone In and Zone From entries indicate the general movement pattern of animal A in the feedlot pen 12 over a period of time. The X and Y coordinate data entries provide detailed movement pattern data concerning animal A over the same period of time.

Once this virtual table is created, the processor 54 executes another routine to compare the virtual table with the physical condition definitions to determine whether the animals exhibit any of the physical conditions of interest as defined by the reference movement pattern data. The reference movement pattern data function as benchmarks against which the animals under observation can be compared. By comparing the virtual table contents with the physical condition definitions, animal health and performance characteristics decisions can be made (block 106).

For example, when the virtual table of FIG. 5c is being compared with the respiratory disorder definition in the physical condition table, the processor 54 determines:

the frequency animal A visited the water zone using the Zone In, Zone From and Time entries;

the duration animal A spent in the water zone using the Zone In and Time entries;

the frequency animal A visited the food zone using the Zone In, Zone From and Time entries;

the duration animal A spent in the food zone using the Zone In and Time entries; and the general overall activity of the animals using the X and Y coordinate data entries.

The calculated values are then compared with the threshold levels in the definition. If the animal meets all of the conditions of the definition, the animal is considered to be suffering a respiratory disorder.

The above process is performed in respect of the animal movement data collected for each of the animals in the feedlot and a comparison between the animal movement data and each of the definitions in the physical condition table is made. The results of the comparisons are displayed via the GUI allowing feedlot owners to identify sick animals, classify other animals according to performance characteristics and take measures to deal with identified production patterns. Animals identified as being sick are generally presented in a list according to disorder. With respect to animals classified according to performance characteristics, the animals can be presented in a list or alternatively the movement patterns of the animals can be presented graphically. With respect to animals classified according to performance characteristics, market ready animals are generally presented in a list, while overfeeding and underfeeding conditions are presented as display screens to the feedlot operator.

In addition to the above, since the movement patterns of the animals in the feedlot 10 are monitored, changes in the overall feeding patterns of the animals can be detected. It is known that the feeding patterns of animals change at each stage in the feedlot as illustrated in Table 1. By detecting changes in feed patterns of animals quickly, operators can apply appropriate protocols for specific animals at appropriate times to optimize processing of the animals through the feedlot. This allows feedlot operators to determine the proper time to implant hormones. This also allows an operator to control the composition and/or amount of feed supplied to the animals which has a three-fold beneficial effect. Firstly, by controlling the composition and/or amount of feed supplied to the animals, feed costs can be reduced. Secondly, in the case of high grade animals, feed can be controlled to inhibit the animals from gaining too much fat and weight which results in penalties for over fat/over large livestock. Lastly, by reducing the number of days the animals are placed on feed and/or by customizing the animals' diet, the animals produce less methane thereby reducing production of greenhouse gas. Although reducing greenhouse gases has an environmental benefit, another advantage exists. Greenhouse gas reductions can be sold as offsets to entities producing significant quantities of greenhouse gases to allow these entities to meet greenhouse gas emission levels. This is achieved by determining the difference in time market ready animals spend in the feedlot with the average industry time an animal spends in a feedlot and estimating the amount of methane gas those animals would have produced over that difference in time.

As one of skill in the art will appreciate, based on the results of animal movement patterns, sick animals can be quickly detected and treated for health problems. Animals showing other similar conditions can be detected and grouped and decisions can be made concerning the optimization of production. After animals under observation have been slaughtered, carcass data can be obtained from the packer and reviewed relative to the definitions to allow the definition reference movement pattern data to be updated. Once the reference movement pattern data has been updated, the current and historical animal movement pattern data can be re-processed in the manner described above using the updated definitions thereby enhancing the accuracy of the present method and system.

In the present embodiment, it is preferred that each animal is fitted with a collar or tag when born. It is also preferred that each rancher, backgrounder and packer includes an interrogator, processor and fixed data collection and transmission unit so that each animal's whereabouts in and duration at a ranch, backgrounder and packer can be tracked. The position data for each animal is collected from the processers at the ranchers, backgrounders, feedlots and packers and is stored in a database. As mentioned previously, the ranchers, backgrounders, feedlots and packers are often at geographically dispersed locations. FIG. 8 shows an example of rancher, backgrounder, feedlot and packer locations.

Tracking an animal generally throughout its lifespace as it is moved from location to location during processing is important especially if the animal is diagnosed with a transmittable disease. Since the animal's previous whereabouts are accurately maintained, the scope of testing to determine other infected animals can be limited to those places where the animal was located and not industry wide.

For example, suppose animal A is diagnosed with a transmittable disease by packer P3. By examining the database, it can be determined that:

the animal was born at ranch R1 and lived there from Mar. 01, 1998 to Sep. 30, 1998;

the animal was moved to the backgrounder B2 and stayed there from Oct. 01, 1998 to May. 01, 1999;

the animal was then moved to feedlot F3 and stayed there from May. 02, 1999 to Nov. 30, 1999; and the animal was moved to packer P3 on Dec. 01, 1999 where it was diagnosed.

Since the animal was diagnosed with a transmittable disease, animals in close proximity to the diseased animals are likely to have contracted the disease. Using the above movement pattern of the animal, all animals that were exposed to the diagnosed animal can be located. Depending on the nature of the disease, the focus of testing can of course vary. For example, if the disease contracted by the animal is one which is normally contracted at a specific age such as 6 months, testing can focus on animals which were exposed to the diseased animal at ranch R1. If the disease is contagious through the animal's life, testing must focus on animals, which were exposed to the diseased animals at Ranch R1, backgrounder B2 and feedlot F3.

In addition, by monitoring each animal's movement, other trends can be identified and pinpointed to a specific ranchers, backgrounders and feedlots. For example, it might be determined that animals born at a particular ranch or prepared at particular backgrounders and feedlots exhibit a trend in terms of grade or other characteristic of interest.

Figure 6:
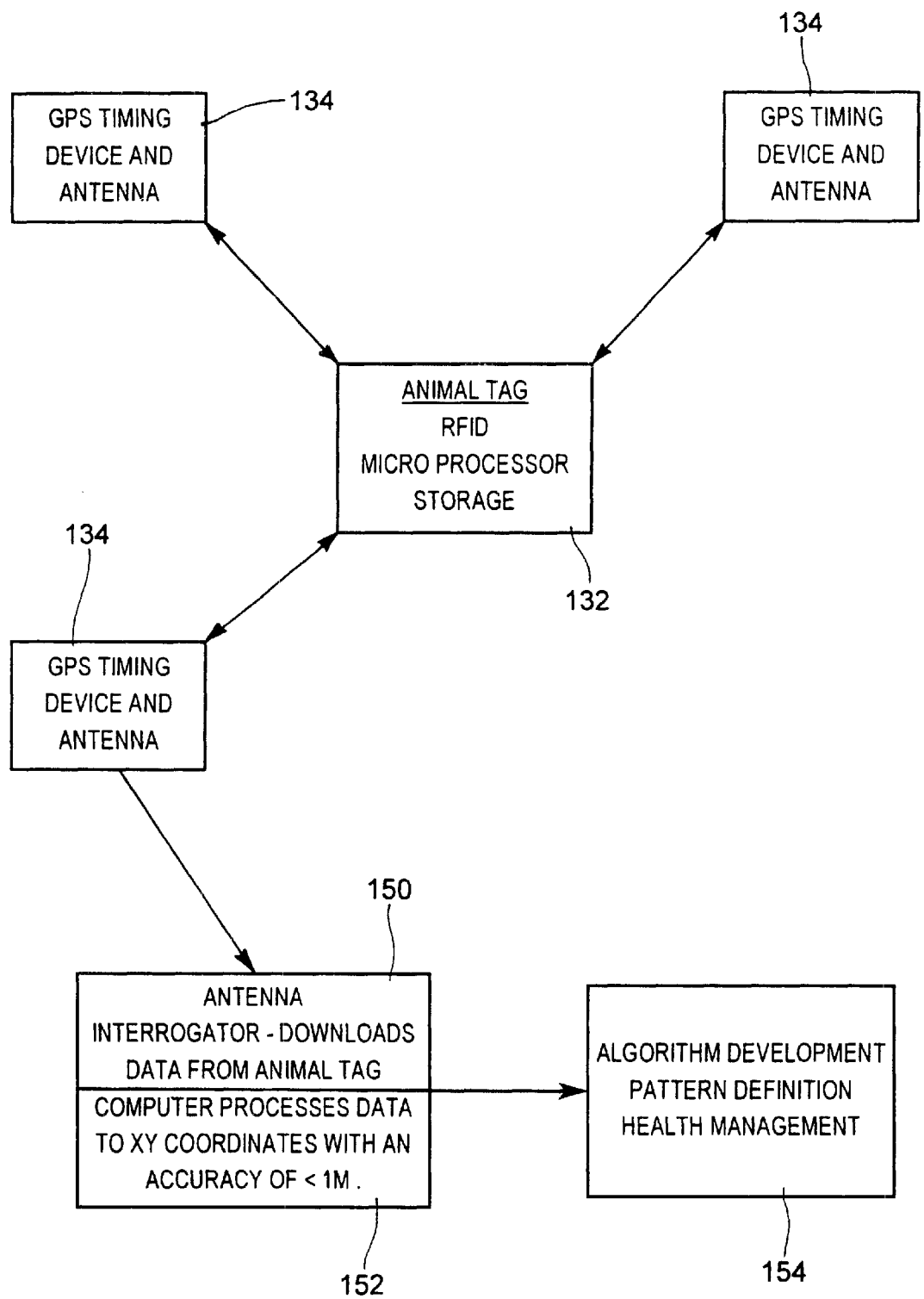
FIG. 6 is an alternative embodiment of a system for feedlot management in accordance with the present invention.

Although the present invention has been described as including data collection and transmission units communicating with GPS satellites to generate raw GPS data, those of skill in the art will appreciate that alternative methods for generating position data can be used. For example, as is shown in FIG. 6, three GPS timing devices 134 can be positioned at various locations in the feedlot 10 with each GPS timing device communicating with RFID animals tags 132 carried by the animals that include data collection and transmission units 32. In this case, raw GPS data is acquired by each GPS timing device. Each GPS timing device 134 in turn sends the raw GPS data to the data collection and transmission units on the RFID animal tags. The data collection and transmission unit in each RFID animal tag records the raw GPS data together with time stamps. When a data collection and transmission unit is polled by the interrogator 150, the data collection and transmission unit sends the raw GPS data and time stamps to the interrogator 150. The interrogator 150 in turn passes the information to the processor 152 which enhances the accuracy of the GPS data and then calculates the XY coordinates of the data collection and transmission unit 32 by triangulation. The data is then downloaded to the processor 154 and processed in the manner described previously.

Alternatively, the animals may be fitted with passive RFID animal tags or bar code tags. In the case of passive RFID animals tags, readers to detect and read the tags to record the animal's locations are required. Similarly, in the case of bar code tags, bar code readers to read the bar codes tags to record the animal's locations are required. These types of tags are more suited to environments where it is simply desired to determine each animal's general location and duration at the location such as at ranches, backgrounders and packers.

Although the system and method for monitoring animal movement patterns within an area have been described specifically with reference to a feedlot environment, those of skill in the art will appreciate that the movement patterns of animals can be monitored in other environments, such as for example in pastures or grazing pens. In this case, the movement patterns of animals can be monitored to determine if the animals suffer from any of the above noted health problems. In addition to the above, definitions including reference movement pattern data modeling the typical movement patterns of animals exhibiting conditions of interest in this environment can be stored in the physical condition table (see Table 2). Typical movement patterns of interest in this environment include but are not limited to:

the movement of animals to a calving zone at inappropriate times indicating the likelihood of reproductive disorders;

the grouping of female animals indicating animals in heat;

the movement of animals along the perimeter of the grazing pen or pasture indicating low food levels; and the grouping of animals at the water zone for long durations indicating poor water quality.

In addition to the above, by monitoring the movement patterns of animals in the pasture or grazing pen, heavily used grazing area can be determined allowing measures to be taken to increase feed in those areas or to move animals to other feeding areas.

The software executed by the processor 54 including the table of FIG. 5b can be downloaded to the processor from a remote location over a network link or can be stored on a physical medium such as a floppy disk or CD-ROM and then loaded onto the processor 54. This allows the software to be supplied to parties having their own animals tracking hardware.

Although particular embodiments of the present invention have been described, those of skill in the art will appreciate that variations and modifications may be made without departing from the spirit and scope thereof as defined by the appended claims.

We claim:

1. A method for tracking the movement of animals as said animals are moved from location to location during processing comprising the steps of:

tagging each animal under observation;

tracking the location of each tagged animal and the duration each tagged animal spends at each location as it is moved to generate movement pattern data representing each tagged animal's movement history; and using the generated data to detect tagged animals that have been in physical proximity with a tagged animal diagnosed with a transmittable disease.

2. The method of claim 1 wherein the generated data representing each tagged animal's movement history represents the tagged animal's movement generally over its lifespan.

3. The method of claim 2 wherein said locations include ranches, backgrounders, feedlots and packers.

4. The method of claim 1 further comprising the step of using the generated data to detect locations that may be the cause of a trend exhibited by specific tagged animals.

5. The method of claim 1 wherein in at least one of said locations, the movement of animals within an area is monitored, said monitoring step comprising the steps of:

collecting positional data of each animal under observation;

processing said positional data to generate data representing the movement patterns of said animals; and analyzing said movement pattern data to determine at least one physical condition of said animals.

6. The method of claim 5 wherein said positional data is collected at intervals.

7. The method of claim 6 wherein during said analyzing step said movement pattern data is compared with reference definitions stored in a database that represent typical movement patterns of animals exhibiting said at least one physical condition.

8. The method of claim 7 wherein said movement pattern data is compared with said reference definitions to detect animals suspected of suffering a health problem.

9. The method of claim 8 wherein said area is divided into at least two zones including a food zone and a water zone and wherein said movement pattern data is compared with said reference definitions to detect the duration and frequency said animals spend in at least one of said zones thereby to determine animals exhibiting said at least one physical condition.

10. The method of claim 9 wherein said movement pattern data is compared with said reference definitions to detect animals exhibiting one or more of the following movement characteristics:

(i) more frequent and longer duration visits to said water zone;

(ii) less frequent visits to said food zone;

(iii) generally overall decreased movement within said area;

(iv) more frequent and shorter duration visits to said water zone; and (v) less frequent and shorter duration visits to said water zone.

11. The method of claim 8 wherein said movement pattern data is compared with said reference definitions to detect animals exhibiting one or both of the following characteristics:

(i) generally little movement within said area; and (ii) circling in one direction.

* * * * *